(12) United States Patent
Donowitz et al.

(10) Patent No.: US 9,850,292 B2
(45) Date of Patent: Dec. 26, 2017

(54) COMPOSITIONS WHICH REGULATE THE EPITHELIAL BRUSH BORDER NA$^+$/H$^+$ EXCHANGER NHE3 AND THEIR METHODS OF USE IN GASTROINTESTINAL DISEASE

(71) Applicants: THE JOHNS HOPKINS UNIVERSITY, Baltimore, MD (US); The Penn State Research Foundation, University Park, PA (US)

(72) Inventors: Mark Donowitz, Baltimore, MD (US); Nicholas Constantine Zachos, Columbia, MD (US); Damian Brett Van Rossum, State College, PA (US); Randen Patterson, University Park, PA (US)

(73) Assignees: The Johns Hopkins University, Baltimore, MD (US); The Penn State Research Foundation, University Park, PA (US)

( * ) Notice: Subject to any disclaimer, the term of this patent is extended or adjusted under 35 U.S.C. 154(b) by 0 days.

(21) Appl. No.: 14/400,904

(22) PCT Filed: May 17, 2013

(86) PCT No.: PCT/US2013/041514
§ 371 (c)(1),
(2) Date: Nov. 13, 2014

(87) PCT Pub. No.: WO2013/173678
PCT Pub. Date: Nov. 21, 2013

(65) Prior Publication Data
US 2015/0139956 A1    May 21, 2015

Related U.S. Application Data

(60) Provisional application No. 61/648,202, filed on May 17, 2012.

(51) Int. Cl.
*C07K 14/47* (2006.01)
*A61K 45/06* (2006.01)
*A61K 35/741* (2015.01)
*A61K 38/17* (2006.01)
*A61K 38/00* (2006.01)

(52) U.S. Cl.
CPC ........ *C07K 14/4705* (2013.01); *A61K 35/741* (2013.01); *A61K 38/1709* (2013.01); *A61K 45/06* (2013.01); *C07K 14/47* (2013.01); *A61K 38/00* (2013.01)

(58) Field of Classification Search
CPC ................................................ C07K 14/4705
See application file for complete search history.

(56) References Cited

U.S. PATENT DOCUMENTS 6,392,025 B1    5/2002    Brant et al.

OTHER PUBLICATIONS

Zachos et al., Phospholipase C-gamma Binds Directly to the Na+/H+ Exchanger 3 and is required for Calcium Regulation of Exchange Activity, The Journal of Biological Chemistry, 284(29): 19437-19444, 2009.*
Donowitz, M. et al., "NHE3 regulatory complexes", J. Exp. Biol, (Jun. 2009), vol. 212 (Pt. 11), pp. 1638-1646.
NCBI, GenBanik Accession No. AAD14402.1, "Na+/H+ exchanger homolog, partial [Oryctolagus cuniculus]" Feb. 10, 1999.
Zachos, N., et al., "A peptide mimicking the NHE3 C-Terminus stimulates basal and blocks CA2+ and cAMP inhibition of NHE3 activity, and prevents cholera toxin-induced mouse jejunal fluid accumulation: potential role as drug therapy for diarrhea", Gastroenterology, (May 2012) vol. 142, No. 5, Supplement 1, p. S-1.
Zizak, M., et al., "Calmodulin kinase II constitutively binds, phosphorylates, and inhibits brush border Na+/H+ exchanger 3 (NHE3) by a NHERF2 protein-dependent process", J. Biol. Chem., Feb. 27, 2012, vol. 287, No. 16, pp. 13442-13456.

* cited by examiner

*Primary Examiner* — Amber D Steele
(74) *Attorney, Agent, or Firm* — Johns Hopkins Technology Ventures

(57) ABSTRACT

A synthetic peptide modeled on the IRCX binding area of NHE3, is a competitive inhibitor of the IRCX and both stimulates basal NHE3 activity and prevents elevated Ca$^{2+}$ and cAMP inhibition of NHE3. Methods of its preparation and use in the prevention and/or treatment of gastrointestinal disease, such as diarrhea are provided.

15 Claims, 5 Drawing Sheets

COMPOSITIONS WHICH REGULATE THE EPITHELIAL BRUSH BORDER NA+/H+ EXCHANGER NHE3 AND THEIR METHODS OF USE IN GASTROINTESTINAL DISEASE

STATEMENT OF GOVERNMENTAL INTEREST

This invention was made with government support under grant nos. DK026523 and GM087410, awarded by the National Institutes of Health. The government has certain rights in the invention.

REFERENCE TO RELATED APPLICATIONS

This application is a 35 U.S.C. §317 U.S. national entry of International Application PCT/US2013/041514, having an international filing date of May 17, 2013, which claims the benefit of U.S. Provisional Application No. 61/648,202, filed May 17, 2012, the content of each of the aforementioned application is herein incorporated by reference in their entirety.

INCORPORATION-BY REFERENCE OF MATERIAL SUBMITTED ELECTRONICALLY

The instant application contains a Sequence Listing which as been submitted in ASCII format via EFS-Web and is hereby incorporated by reference in its entirety. Said ASCII copy, created on May 8, 2013, is named P11498-03_ST25.txt and is 762 bytes in size.

BACKGROUND OF THE INVENTION

Bacterial diarrhea is a major world health problem and one of the leading killers of children in the developing world. It is estimated that 1.9 million children worldwide die every year due to complications from enteropathogenic bacterial infection.

Bacterial diarrhea infections are prominent in developing nations and their impact has dramatically increased in the past decades in industrialized countries due to increase food processing, and due to the ease of worldwide travel. Virulent strains of *Escherichia coli* (*E. coli*) such as enteropathogenic *E. coli* (EPEC), enterotoxigenic *E. coli* (ETEC), enterinvasive *E. coli* (EIEC) and enterohemorrhagic *E. coli* (EHEC) are responsible for a significant proportion of bacterial enteric infections. While infections with EPEC cause infantile diarrhea, EHEC, an emerging zoonotic pathogen causes diarrhea that can lead to hemorrhagic colitis and hemolytic uremic syndrome. EPEC, ETEC, EIEC and EHEC, as well as other known bacterial pathogens, such as *Salmonella* and *Shigella*, for example, remain serious threats to human health. Of importance is that rotaviral diarrhea is at top of list of fatal diarrheal diseases.

Diarrheal diseases are the second leading cause of infant mortality world-wide. They kill due to dehydration from intestinal loss of water and electrolytes. A critical lack in current diarrheal therapy is availability of a drug that can stimulate intestinal $Na^+$ absorption. In the human small intestine, the $Na^+/H^+$ Exchanger Isoform 3 (NHE3) protein accounts for the majority of $Na^+$ absorption and is inhibited in both inflammatory and enterotoxigenic diarrheas. While chloride secretion leads to massive fluid loss in some diarrheal diseases such as cholera, inhibition of Na absorptions occurs in almost all diarrheal diseases.

There still exists, therefore, an unmet need for improved treatments for gastrointestinal diseases such as diarrhea.

SUMMARY OF THE INVENTION

In accordance with an embodiment, the present invention provides a sodium/hydrogen Exchanger 3 (NHE3) Inhibitory Regulatory Complex ICRX Competing Peptide (ICRX-CP), or a functional portion or analog or derivative thereof.

In accordance with another embodiment, the present invention provides a ICRX-CP comprising the amino acid sequence of NVDFSTPRPSTVEASVSYLLRESASAV-CLDMQSLEQRR (SEQ ID NO: 1), or a functional portion or analog or derivative thereof.

In accordance with still another embodiment, the present invention provides a peptide heretofore described above, wherein the peptide stimulates basal NHE3 activity and prevents elevated $Ca^{2+}$ and cAMP inhibition of NHE3.

In accordance with a further embodiment, the present invention provides a pharmaceutical composition comprising the peptide heretofore described above, and a pharmaceutically acceptable carrier.

In accordance with an embodiment, the present invention provides a pharmaceutical composition comprising the peptide heretofore described above, and a second therapeutic agent, and a pharmaceutically acceptable carrier.

In accordance with a further embodiment, the present invention provides a method of treatment of a gastrointestinal disease in a subject comprising administering to the subject the ICRX-CP peptides described herein, or the pharmaceutical compositions described herein, in an effective amount to modulate or treat the gastrointestinal disease.

In accordance with an embodiment, the present invention provides the use of the ICRX-CP peptide heretofore described above, in preparation of a medicament, preferably a medicament for use in treatment of a gastrointestinal disease in a mammal.

In accordance with another embodiment, the present invention provides the use of an effective amount of the ICRX-CP peptide heretofore described above, and an effective amount of a probiotic composition comprising one or more strains of probiotic microorganisms in preparation of a medicament, preferably a medicament for use in the prevention or treatment of a gastrointestinal disease in a mammal.

BRIEF DESCRIPTION OF THE DRAWINGS

FIG. 1A is an illustration showing domain organization of NHE3 (transport, N terminus and regulatory, C terminus) with proteins shown to bind to the C-terminus and highlighting the SRCX and IRCX. FIG. 1B is a model of known IRCX components (NHERFs1-4, CaMKII, CK2, PLCγ) under basal conditions and after elevated $Ca^{2+}$ showing dynamic complexes assembled on the C-terminus acting as a dimer.

Figure 4:
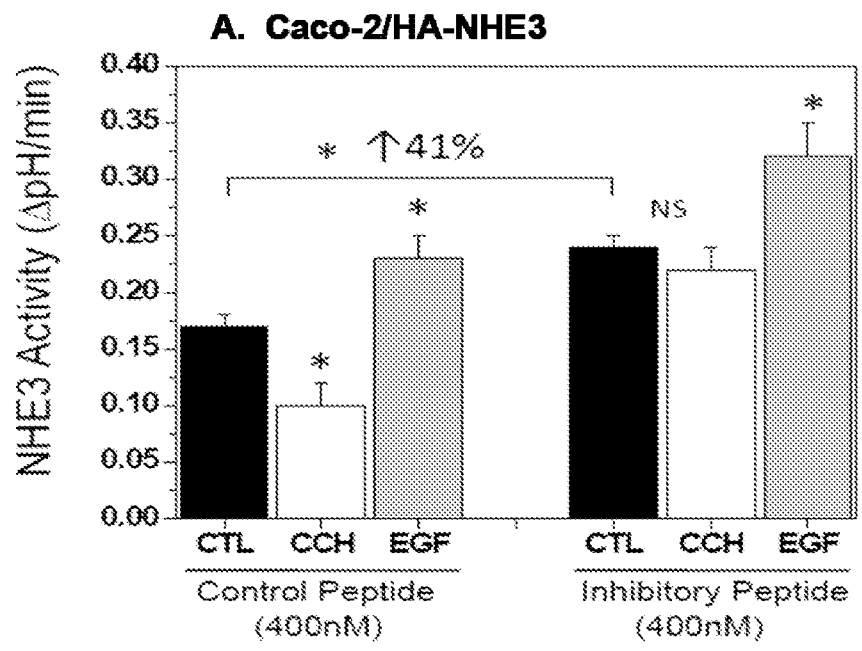
Figure 4:
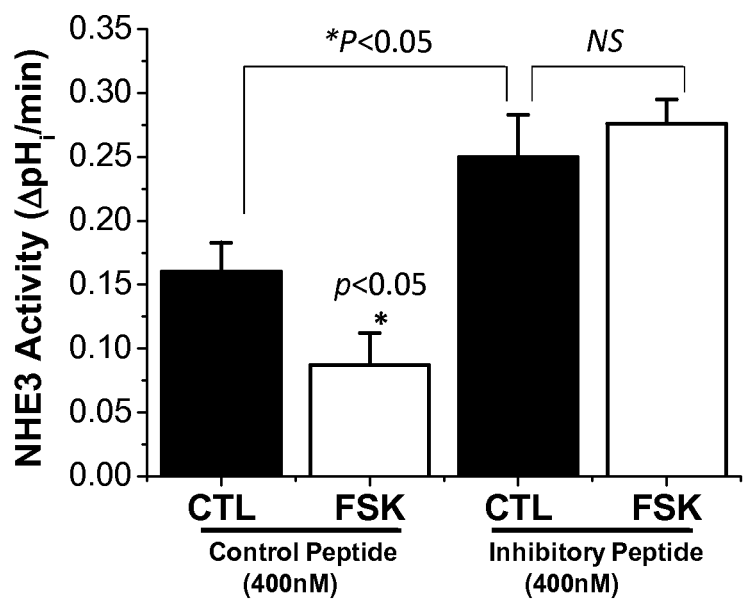

FIG. 4A is a bar graph depicting the results when Caco-2/HA-NHE3 cells were exposed to IRCX-CP (400 nM) for 15 minutes then basal, carbachol (cch) (10 µM) inhibited and EGF (200 ng/ml) stimulated NHE3 were determined (n=4). FIG. 4B is another bar graph depicting the effects when mouse jejunum was exposed in vitro to IRCX-CP (400 nM) and/or forskolin (10 µM) for 15 minutes with NHE3 activity determined by BCECF.

Figure 5:
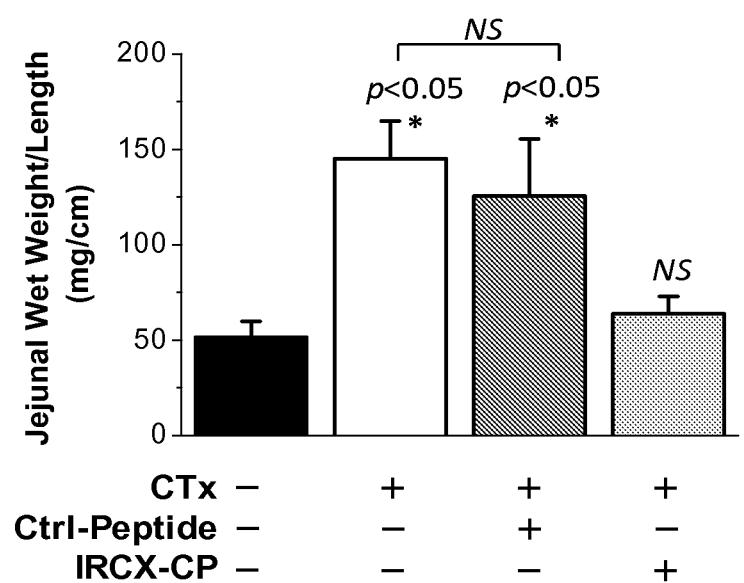

FIG. 5 is a bar graph depicting mouse jejunum exposed in vivo to cholera toxin (1 µg) with, or without IRCX-CP (400 nM)) for 6 hours. *p<0.05 vs. control.

DETAILED DESCRIPTION OF THE INVENTION

Figure 1:
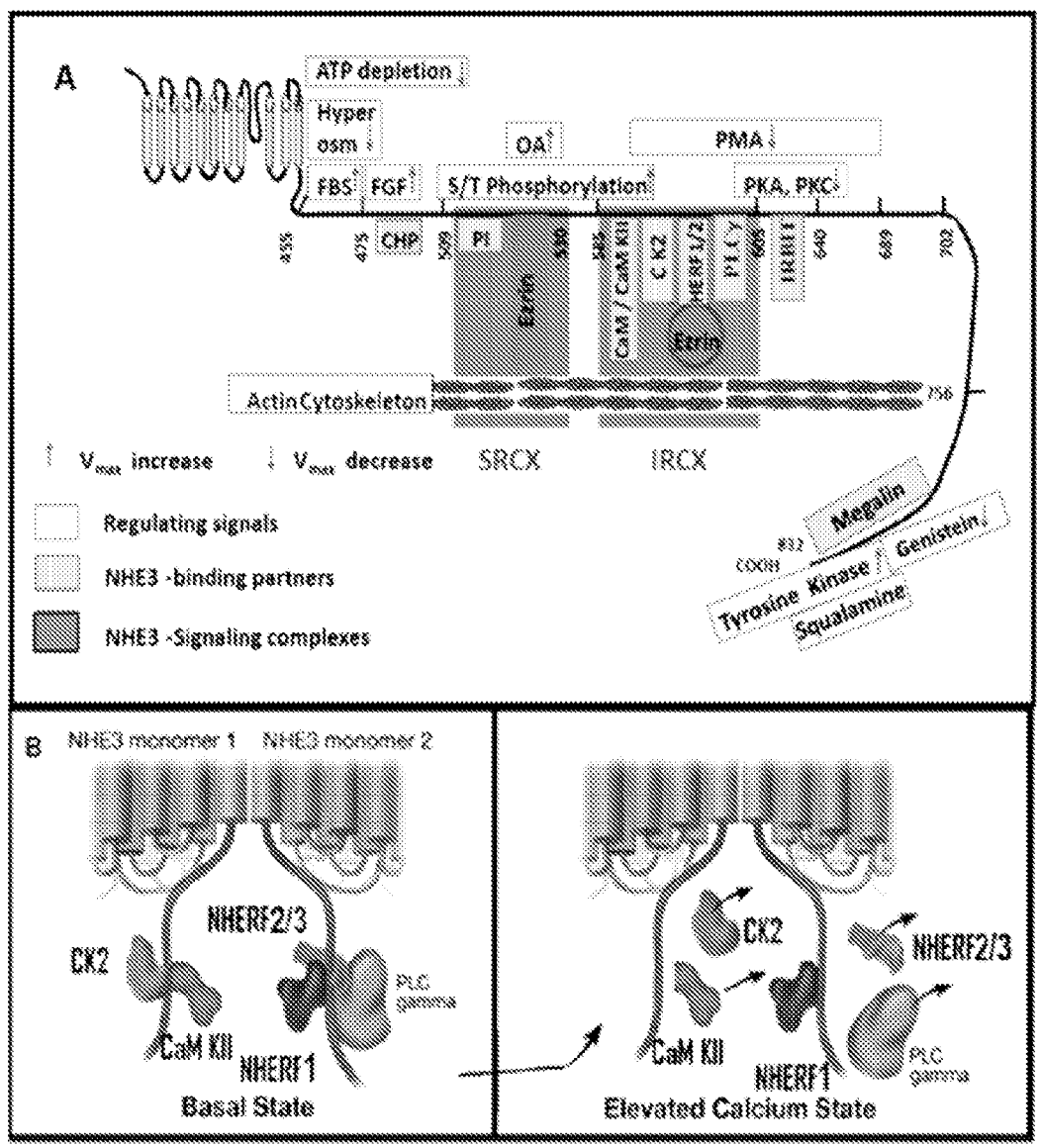
FIG. 1 depicts NHE3 Complexes.

The present inventors have now found that under basal conditions, intestinal NHE3 is functionally active in $Na^+$ absorption. Immediately post prandially, NHE3 is inhibited, producing increased luminal water that spreads digestive enzymes over the absorptive surface; later in digestion, NHE3 is stimulated to prevent dehydration. Both up- and down-regulation of NHE3 occurs mostly via changes in its rates of exocytosis and/or endocytosis. Exaggeration of the latter contributes to the pathogenesis of most diarrheal diseases. The ion-translocation pathway of NHE3 is formed by the transmembrane segments, while the intracellular C-terminus is necessary for regulation of NHE3 activity and trafficking (FIG. 1).

The C-terminus acts as a platform for assembly of the Inhibitory Regulatory Complex (IRCX). The IRCX is formed at amino acids 568-605 and accounts for the PI 3-K dependent part of basal NHE3 activity, acutely inhibited NHE3 activity (cAMP, cGMP, $Ca^{2+}$), as well as the association of NHE3 with the microvillar actin cytoskeleton, a newly recognized, dynamic aspect of NHE3 regulation. The ICRX complex forms at areas in which NHE3 associates with the actin cytoskeleton (FIG. 1). Interaction of IRCX with ezrin and actin requires the NHERF family of multi-PDZ domain proteins.

In accordance with an embodiment, the present invention provides a sodium/hydrogen Exchanger 3 (NHE3) Inhibitory Regulatory Complex ICRX Competing Peptide (ICRX-CP), or a functional portion or analog or derivative thereof.

In accordance with an embodiment, the present invention provides an ICRX-CP comprising the amino acid sequence of NVDFSTPRPSTVEASVSYLLRESASAVCLD-MQSLEQRR (SEQ ID NO: 1), or a functional portion or analog or derivative thereof.

In accordance with another embodiment, the present invention provides a peptide heretofore described above, wherein the peptide binds NHE3 IRCX binding domain or functional portion or fragment thereof.

In accordance with a further embodiment, the present invention provides a peptide heretofore described above, comprising amino acids 568-605 of the NHE3 protein, or a functional portion or fragment thereof.

In accordance with still another embodiment, the present invention provides a peptide heretofore described above, wherein the peptide stimulates basal NHE3 activity and prevents elevated $Ca^{2+}$ and cAMP inhibition of NHE3.

In accordance with an embodiment, the present invention provides a pharmaceutical composition comprising the peptide heretofore described above, and a pharmaceutically acceptable carrier.

In accordance with another embodiment, the present invention provides a pharmaceutical composition comprising the peptide heretofore described above, and a second therapeutic agent, and a pharmaceutically acceptable carrier.

It will be understood that in accordance with an embodiment, the second therapeutic agent is selected from the group consisting of: electrolyte solutions, antibiotics, antihelminths, antiparisitcals, bulking agents, absorbents, anti-inflammatory drugs, zinc supplements and opioids.

In accordance with another embodiment, the present invention provides a method of treatment of a gastrointestinal disease in a subject comprising administering to the subject the ICRX-CP peptides described herein, or the pharmaceutical compositions described herein, in an effective amount to modulate or treat the gastrointestinal disease.

In accordance with another embodiment, the gastrointestinal diseases treated using the peptides and methods of the present invention includes infections of the gut, including, for example, cholera, dysentery, *Giardia*, EPEC, ETEC, EIEC and EHEC, as well as other known bacterial pathogens, such as *Salmonella* and *Shigella*, and rotavirus; also viral, parasitic, chemical causes of diarrhea. In addition this could be used for all causes of diarrhea, including but not limited to, chronic diarrhea such at IBS, IBD, radiation bowel disease, celiac disease, B12 deficiency and many others.

In accordance with another embodiment, the present invention provides the use of the ICRX-CP peptide heretofore described above, in preparation of a medicament, preferably a medicament for use in treatment of a gastrointestinal disease in a mammal.

For example, the medicament for use in treatment of a gastrointestinal disease can include the ICRX-CP peptide heretofore described above and an antibiotic. Examples of antibiotic agents suitable for use in pharmaceutical composition comprising a peptide heretofore described above and one or more antibiotic agents include, for example, quinolone antibiotics, such as levofloxacin, ciprofloxacin, ibafloxacin, pradofloxacin, rosoxacin, and sarafloxacin. Other suitable antibiotics are trimethoprim-sulfamethoxazole mixtures such as Bactrim®. Alternatives include rifaximin and azithromycin. Dosages vary with the weight and age of the subject to be treated. Typically, quinolone antibiotics and trimethoprim-sulfamethoxazole mixtures are given at dosages between 250 and 500 mg daily. For trimethoprim-sulfamethoxazole, the dosages are generally between about 5 mg/kg and 25 mg/kg. For rifaximin the dosage ranges from 100 mg to about 500 mg, with 200 mg being preferred. Azithromycin is typically administered at 250-500 mg/day. The dosages required are well within the knowledge of those of ordinary skill in the art.

Probiotics are live microbes which, when administered to man or animals, promote the well-being of the host by improving the intestinal microbial balance (Fuller, R. Probiotics in man and animals, 1989, J. Appl. Microbiol. 66:365-378). The best-documented probiotics include *L. rhamnosus* LGG, *L. johnsonii* LAI, *L. casei* Shirota and *Bifidobacterium lactis* Bbl2. In addition, a number of other probiotics have been described in the literature of the art (see for example M. E. Sanders & J. H. in't Veld 1999. Antonie van Leeuwenhoek 76:293-315, Kluwer Academic Publishers). The health-promoting effects of probiotics include the balancing and maintenance of intestinal flora, prevention or treatment of diarrhea, stimulation of the immune system and anti-carcinogenic activity. The useful effects of probiotics in human intestines are based on several factors caused by live bacterial cells, their cell structures and metabolic products. Probiotics are usually administered in nutrients or as capsules.

A probiotic strain or strains used in the compositions and methods of the present invention may be selected from a group comprising yeasts, preferably the genus *Saccharomyces*, moulds, preferably the genus *Aspergillus*, bacteria, preferably the genus *Lactobacillus, Bifidobacterium, Streptococcus, Enterococcus*, and a mixture thereof. For example, strains from the species *Lactobacillus johnsonii, Bifidobacterium lactis, Streptococcus thermophilus*, or, *Lactobacillus paracasei* may be used. For example, if bacterial probiotics are to be produced, strains may be selected from the geni *Lactobacillus, Streptococcus, Bifidobacterium, Bacteroides, Clostridium, Fusobacterium, Nelissococcus, Propionibacterium, Enterococcus, Lactococcus, Staphylococcus, Peptostreptococcus, Bacillus, Pediococcus, Micrococcus, Leuconostoc, Weissella, Aerococcus, Oenococcus*.

The known benefits of enteral administration of probiotic microorganisms include enhanced host defense to disease, improving colonization resistance of the harmful microflora and numerous other areas of health promotion such as prevention and/or treatment of diarrhea. Probiotics have been suggested to play an important role in the formation or establishment of a well-balanced, indigenous, intestinal microflora in newborn children or adults receiving high doses of antibiotics.

As such, in accordance with another embodiment, the present invention provides the use of an effective amount of the ICRX-CP peptide heretofore described above, and an effective amount of a probiotic composition comprising one or more strains of probiotic microorganisms in preparation of a medicament, preferably a medicament for use in the prevention and/or treatment of a gastrointestinal disease in a mammal.

In accordance with a further embodiment, the present invention provides a method for the prophylaxis and/or treatment of a gastrointestinal disorder in a subject comprising administering to the subject a composition comprising an effective amount of the ICRX-CP peptide described herein and an effective amount of a probiotic composition comprising one or more strains of probiotic microorganisms.

The probiotic composition used in the present invention can be in a solid, liquid or powder formulation and can comprise between $10^5$ to $10^{10}$ colony forming units of probiotic microorganisms in an acceptable carrier.

The compositions and methods according to this invention can also be accomplished through the administration of a powder per se or in the form of a capsule, pill or tablet which incorporates the ICRX-CP peptide and the proper level and types of probiotics disclosed herein. Also contemplated within the scope of this invention is the administration of the probiotic system in a nutritional product. This nutritional product may be, for example, powdered milk, a commercially available infant formula or powdered nutritional supplements. Thus, one aspect of this invention includes the mixing of the ICRX-CP peptide and the probiotics with a preformed liquid nutritional product (i.e. milk or commercial infant formula). The present invention also contemplates a powdered nutritional product which may be a complete nutritional product or a nutritional supplement comprising vitamins and minerals in conjunction with the ICRX-CP peptide and probiotics. Thus, in one embodiment invention includes a powdered formulation containing at least one or more probiotic organisms at levels which would deliver the minimum colony forming units (CFU's) during a typical day of feeding and an effective amount of the ICRX-CP peptide.

NHE3 is inhibited in both inflammatory and enterotoxigenic diarrheas. Characterization of a small NHE3 peptide, which stimulates NHE3 activity and also blocks $Ca^{2+}$ and cAMP inhibition of NHE3 in cells and intact intestine, represents an important step towards developing a new drug to treat diarrhea.

The term, "amino acid" includes the residues of the natural α-amino acids (e.g., Ala, Arg, Asn, Asp, Cys, Glu, Gln, Gly, His, Hyl, Ile, Leu, Met, Phe, Pro, Ser, Thr, Trp, Tyr, and Val) in D or L form, as well as β-amino acids, synthetic and unnatural amino acids. Many types of amino acid residues are useful in the adipokine polypeptides and the invention is not limited to natural, genetically-encoded amino acids. Examples of amino acids that can be utilized in the peptides described herein can be found, for example, in Fasman, 1989, CRC Practical Handbook of Biochemistry and Molecular Biology, CRC Press, Inc., and the reference cited therein. Another source of a wide array of amino acid residues is provided by the website of RSP Amino Acids LLC.

The term, "peptide," as used herein, includes a sequence of from four to sixteen amino acid residues in which the α-carboxyl group of one amino acid is joined by an amide bond to the main chain (α- or β-) amino group of the adjacent amino acid. The peptides provided herein for use in the described and claimed methods and compositions can be cyclic.

The term, "amount effective to treat diarrhea" is that amount effective to treat, ameliorate, or prevent acute and prolonged (<1 month) or chronic (>1 month) diarrhea or symptoms thereof, or to exhibit a detectable therapeutic or preventative effect.

The precise effective amount for a human subject will depend upon the severity of the subject's disease state, general health, age, weight, gender, diet, time and frequency of administration, drug combination(s), reaction sensitivities, and tolerance or response to therapy. A routine experimentation can determine this amount and is within the judgment of the medical professional. Compositions may be administered individually to a patient, or they may be administered in combination with other drugs, hormones, agents, and the like.

With respect to peptide compositions described herein, the carrier can be any of those conventionally used, and is limited only by physico-chemical considerations, such as solubility and lack of reactivity with the active compound (s), and by the route of administration. The carriers described herein, for example, vehicles, adjuvants, excipients, and diluents, are well-known to those skilled in the art and are readily available to the public. It is preferred that the carrier be one which is chemically inert to the active agent(s), and one which has little or no detrimental side effects or toxicity under the conditions of use. Examples of the carriers include soluble carriers such as known buffers which can be physiologically acceptable (e.g., phosphate buffer) as well as solid compositions such as solid-state carriers or latex beads.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, or suspensions. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

It will be appreciated by one of skill in the art that, in addition to the above-described pharmaceutical compositions, the ICRX-CP of the invention can be formulated as inclusion complexes, such as cyclodextrin inclusion complexes, or liposomes.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In one or more preferred embodiments, the route of administration of the above-described pharmaceutical compositions, the ICRX-CP of the invention is oral.

In addition, in an embodiment, the compositions comprising ICRX-CP or derivatives thereof, may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular peptide containing compositions, as well as by the particular method used to administer the composition. Accordingly, there are a variety of suitable formulations of the pharmaceutical compositions of the invention. The following formulations for parenteral, subcutaneous, intravenous, intramuscular, intraarterial, intrathecal and interperitoneal administration are exemplary, and are in no way limiting. More than one route can be used to administer the compositions of the present invention, and in certain instances, a particular route can provide a more immediate and more effective response than another route.

Injectable formulations are in accordance with the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

As used herein the term "pharmaceutically active compound" or "therapeutically active compound" means a compound useful for the treatment or modulation of a disease or condition in a subject suffering therefrom. Examples of pharmaceutically active compounds can include any drugs known in the art for treatment of disease indications.

Other therapeutically active compounds included in the pharmaceutical compositions suitable for use in the methods of the present invention include antidiarrheal agents. Examples of such agents include, but are not limited to: bulking agents like methylcellulose, guar gum, kaolin suspensions or plant fiber (bran, sterculia, isabgol, etc.) are used for diarrhea in functional bowel disease and to control ileostomy output; absorbents which absorb toxic substances that cause infective diarrhea, such as methylcellulose; anti-inflammatory solutions, such as bismuth subsalicylate; and opioids, such as loperamide and diphenoxylate.

For purposes of the present invention, the term "diarrhea," as used herein means frequent, poorly formed, loose, watery stools of a subject. A subject having diarrhea means the subject is passing loose stools at least three times a day. The term "acute diarrhea" is a common problem that usually lasts <7 days but can last in a protracted or prolonged form for <21 days. Diarrhea lasting more than 2 days is often a sign of an enteropathogenic infection. The term "chronic diarrhea" means diarrhea that lasts at least 4 weeks. Chronic diarrhea symptoms may be continual or intermittent. The term "traveler's diarrhea" means diarrheal symptoms associated with travel-related infection. It may be caused by many different organisms, including bacteria such as *E. coli, Salmonella, Shigella, Campylobacter, Aeromonas, Plesiomonas*, and *vibrios*; parasites such as *Giardia, Entamoeba histolytica, Cryptosporidium*, and *Cyclospora*; and viruses. In addition to diarrhea, symptoms may include nausea, vomiting, abdominal pain, fever, sweats, chills, headache, and malaise. Diarrhea may also be the result of food borne enteropathogens. Typical food borne pathogens are *E. coli, Salmonella, Shigella, Yersinia*, and *Campylobacter*.

Diarrhea of any duration may cause dehydration, which means the body lacks enough fluid and electrolytes—chemicals in salts, including sodium, potassium, and chloride—to function properly. Loose stools contain more water and electrolytes and often weigh more than solid stools.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of diarrhea in a mammal. Furthermore, the treatment or prevention provided by the inventive method can include treatment or prevention of one or more conditions or symptoms of the disease, e.g., diarrhea, being treated or prevented. Also, for purposes herein, "prevention" can encompass delaying the onset of the disease, or a symptom or condition thereof.

In accordance with an embodiment of the present invention, the medicament for treating a disease in a subject can encompass many different formulations known in the pharmaceutical arts, including, for example, intravenous and sustained release formulations. With respect to the inventive methods, the disease can include any gastrointestinal disease, for example, diarrheal diseases.

As used herein, the term "treat," as well as words stemming therefrom, includes diagnostic and preventative as well as disorder remitative treatment.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

An effective amount of ICRX-CP or derivatives thereof, to be employed therapeutically will depend, for example, upon the therapeutic and treatment objectives, the route of administration, the age, condition, and body mass of the subject undergoing treatment or therapy, and auxiliary or adjuvant therapies being provided to the subject. Accordingly, it will be necessary and routine for the practitioner to titer the dosage and modify the route of administration, as required, to obtain the optimal therapeutic effect. A typical daily dosage might range from about 0.1 mg/kg to up to about 100 mg/kg or more, preferably from about 0.1 to about 10 mg/kg/day depending on the above-mentioned factors. Typically, the clinician will administer antibody until a dosage is reached that achieves the desired effect. The progress of this therapy is easily monitored by conventional assays.

While the ICRX-CP or derivatives thereof are generally water soluble, they can be modified into a depot form, such that the manner in which the ICRX-CP is released into the body to which it is administered is controlled with respect to time and location within the body (see, for example, U.S. Pat. No. 4,450,150). Depot forms of ICRX-CP or derivatives thereof can be, for example, an implantable composition comprising the ICRX-CP or derivatives thereof and a porous or non-porous material, such as a polymer, wherein the ICRX-CP or derivatives thereof is encapsulated by or diffused throughout the material and/or degradation of the non-porous material. The depot is then implanted into the desired location within the body and the ICRX-CP or derivatives thereof are released from the implant at a pre-determined rate.

The dosage ranges for the administration of ICRX-CP or derivatives thereof, are those large enough to produce the desired effect in which the symptoms of the malignant disease are ameliorated. The dosage should not be so large as to cause adverse side effects, such as unwanted cross-reactions, anaphylactic reactions, and the like. Generally, the dosage will vary with the age, condition, sex and extent of disease of the patient and can be determined by one of skill in the art. The dosage can be adjusted by the individual physician in the event of any complication.

Generally, when ICRX-CP or derivatives thereof, are administered together with additional therapeutic agents, lower dosages can be used. ICRX-CP or derivatives thereof, can be administered parenterally by injection or by gradual perfusion over time. ICRX-CP or derivatives thereof, can be administered intravenously, intraperitoneally, intramuscularly, subcutaneously, intracavity, or transdermally, alone or in combination with effector cells. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

In reference to the parent ICRX-CP, the functional portion can comprise, for instance, about 90%, 95%, or more, of the parent ICRX-CP.

The functional portion of the ICRX-CP can comprise additional amino acids at the amino or carboxy terminus of the portion, or at both termini, which additional amino acids are not found in the amino acid sequence of the parent ICRX-CP. Desirably, the additional amino acids do not interfere with the biological function of the functional portion.

Included in the scope of the invention are functional variants of the inventive polypeptides, and proteins described herein. The term "functional variant" as used herein refers to ICRX-CP, polypeptide, or protein having substantial or significant sequence identity or similarity to ICRX-CP, polypeptide, or protein, which functional variant retains the biological activity of ICRX-CP, polypeptide, or protein of which it is a variant. In reference to the parent ICRX-CP, polypeptide, or protein, the functional variant can, for instance, be at least about 30%, 50%, 75%, 80%, 90%, 98% or more identical in amino acid sequence to the parent ICRX-CP, polypeptide, or protein.

The functional variant can, for example, comprise the amino acid sequence of the parent ICRX-CP, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Functional variants can also include extensions of the parent ICRX-CP polypeptide. For example, a functional variant of the ICRX-CP polypeptide can include 1, 2, 3, 4 and 5 additional amino acids from either the N-terminal or C-terminal end of the ICRX-CP polypeptide.

Alternatively or additionally, the functional variants can comprise the amino acid sequence of the parent ICRX-CP, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent ICRX-CP, polypeptide, or protein.

The ICRX-CP, polypeptide, or protein can consist essentially of the specified amino acid sequence or sequences described herein, such that other components of the functional variant, e.g., other amino acids, do not materially change the biological activity of the functional variant.

ICRX-CP, polypeptides, and proteins of the invention (including functional portions and functional variants) of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

ICRX-CP, polypeptides, and proteins of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

When ICRX-CP, polypeptides, and proteins of the invention (including functional portions and functional variants) are in the form of a salt, preferably, the polypeptides are in the form of a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

ICRX-CP, polypeptide, and/or protein of the invention (including functional portions and functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; and U.S. Pat. No. 5,449,752. Also, polypeptides and proteins can be recombinantly produced using the nucleic acids described herein using standard recombinant methods. See, for instance, Sambrook et al., *Molecular Cloning: A Laboratory Manual*, $3^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. Further, some of the ICRX-CP s, polypeptides, and proteins of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, ICRX-CP, polypeptides, and/or proteins described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive TCRs, polypeptides, and proteins can be synthetic, recombinant, isolated, and/or purified.

Included in the scope of the invention are conjugates, e.g., bioconjugates, comprising any of the inventive ICRX-CP, polypeptides, or proteins (including any of the functional portions or variants thereof), nucleic acids, recombinant expression vectors, host cells, populations of host cells, or antibodies, or antigen binding portions thereof. Conjugates, as well as methods of synthesizing conjugates in general, are known in the art (See, for instance, Hudecz, F., *Methods Mol. Biol.* 298: 209-223 (2005) and Kirin et al., *Inorg Chem.* 44(15): 5405-5415 (2005)).

Polynucleotides encoding full length ICRX-CP or biologically active C-terminal fragments are included herein. Further, the invention provides ICRX-CP polynucleotide sequences encoding a ICRX-CP polypeptide or C-terminal biologically active fragment thereof as described herein of at least about 60%, 65%, 70%, 75%, 80%, 85%, 90% or 95% identical to murine ICRX-CP or C-terminal fragment rabbit NHE3 aa 568-605 (e.g., SEQ ID NO: 1).

Minor modifications of the ICRX-CP primary amino acid sequence can result in proteins which have substantially equivalent activity as compared to the exemplified ICRX-CP polypeptides. Such modifications can be deliberate, such as modification introduced by a method such as site-directed mutagenesis, truncations, or can be spontaneous. All of the polypeptides produced by these modifications are encompassed within the present invention, provided polypeptide maintains a function of ICRX-CP, as disclosed herein. Deletion of one or more amino acids can also result in a modification of the structure of the resultant molecule without significantly altering its biological activity. This can lead to the development of a smaller active molecule which would have broader utility. For example, one can remove amino or carboxy terminal amino acids which are not required for the biological activity or other function of ICRX-CP.

Further provided by the invention is a nucleic acid comprising a nucleotide sequence encoding the ICRX-CP, polypeptides, or proteins described herein (including functional portions and functional variants thereof).

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The invention also provides substituted nucleic acid sequences which encode any of the substituted ICRX-CPs, substituted polypeptides, substituted proteins, or substituted functional portions or functional variants thereof.

In some embodiments, the substituted nucleic acid sequence may be optimized. Without being bound to a particular theory, it is believed that optimization of the nucleic acid sequence increases the translation efficiency of the mRNA transcripts. Optimization of the nucleic acid sequence may involve substituting a native codon for another codon that encodes the same amino acid, but can be translated by tRNA that is more readily available within a cell, thus increasing translation efficiency. Optimization of the nucleic acid sequence may also reduce secondary mRNA structures that would interfere with translation, thus increasing translation efficiency.

The polynucleotide sequence encoding a ICRX-CP polypeptide of the invention includes the exemplified sequences, as well as conservative variations of the exemplified polypeptide sequences. The term "conservative variation" as used herein refers to a replacement of an amino acid residue by another, biologically similar amino acid residue. The term "conservative variation" also includes the use of a substituted amino acid in place of an unsubstituted parent amino acid, provided that an antibody that specifically interacts with the substituted polypeptide also is specifically immunoreactive with the unsubstituted polypeptide.

As a non-limiting example, a conservative variant can be a sequence in which a first uncharged polar amino acid is conservatively substituted with a second (non-identical) uncharged polar amino acid such as cysteine, serine, threonine, tyrosine, glycine, glutamine or asparagine or an analog thereof. A conservative variant also can be, for example, a sequence in which a first basic amino acid is conservatively substituted with a second basic amino acid such as arginine, lysine, histidine, 5-hydroxylysine, N-methyllysine or an analog thereof. Similarly, a conservative variant can be, for example, a sequence in which a first hydrophobic amino acid is conservatively substituted with a second hydrophobic amino acid such as alanine, valine, leucine, isoleucine, proline, methionine, phenylalanine or tryptophan or an analog thereof. In the same way, a conservative variant can be, for example, a sequence in which a first acidic amino acid is conservatively substituted with a second acidic amino acid such as aspartic acid or glutamic acid or an analog thereof; a sequence in which an aromatic amino acid such as phenylalanine is conservatively substituted with a second aromatic amino acid or amino acid analog, for example, tyrosine; or a sequence in which a first relatively small amino acid such as alanine is substituted with a second relatively small amino acid or amino acid analog such as glycine or valine or an analog thereof.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive ICRX-CP peptides. It is generally appreciated that conditions can be rendered more stringent by the addition of increasing amounts of formamide.

A polynucleotide of the invention can be obtained by several methods. For example, the polynucleotide can be isolated using hybridization or computer-based techniques which are well known in the art. These include, but are not limited to: 1) hybridization of genomic or cDNA libraries with probes to detect homologous nucleotide sequences; 2)

antibody screening of expression libraries to detect cloned DNA fragments with shared structural features; 3) polymerase chain reaction (PCR) on genomic DNA or cDNA using primers capable of annealing to the DNA sequence of interest; 4) computer searches of sequence databases for similar sequences; and 5) differential screening of a subtracted DNA library.

In certain exemplary embodiments, vectors such as, for example, expression vectors, containing a nucleic acid encoding one or more ICRX-CP polypeptides described herein are provided. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably. However, the invention is intended to include such other forms of expression vectors, such as viral vectors (e.g., replication defective retroviruses, adenoviruses and adeno-associated viruses), which serve equivalent functions.

In certain exemplary embodiments, the recombinant expression vectors comprise a nucleic acid sequence (e.g., a nucleic acid sequence encoding one or more ICRX-CP polypeptides or fragments thereof described herein) in a form suitable for expression of the nucleic acid sequence in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence encoding one or more ICRX-CP polypeptides is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences, e.g., adipose tissue). It will be appreciated by those skilled in the art that the design of the expression vector can depend on such factors as the choice of the host cell to be transformed, the level of expression of protein desired, and the like. The expression vectors described herein can be introduced into host cells to thereby produce proteins or portions thereof, including fusion proteins or portions thereof, encoded by nucleic acids as described herein (e.g., ICRX-CP).

EXAMPLES

Cell Culture. Studies were performed using either PS120 fibroblasts stably transfected with rabbit NHE3 (rNHE3) or Caco-2BBe cells transiently infected (Adenovirus) with rNHE3. PS 120 cells which lack all endogenous plasma membrane NHEs were stably transfected with rNHE3 tagged either at the C terminus with a vesicular stomatitis virus-glycoprotein epitope tag (NHE3V) or on the N-terminus with a triple HA epitope tag (HA-NHE3), as described (J. Biol. Chem. 281, 17845-17855 (2006)). They were transfected as described previously (id., Am. J. Physiol. 270, G29-G41 (1996)). Where indicated, PS120/HA-NHE3 or PS120/NHE3V cells were stably co-transfected with human NHERF1 or NHERF2, as previously described (J. Biol. Chem. 273, 29972-29978 (1998)). All stable PS120 cell lines were maintained at 37° C. in a humidified atmosphere with 5% $CO_2$ and 95% $O_2$ in Dulbecco's modified Eagle's medium with Na pyruvate (#10-013-CV, Mediatech.Inc) supplemented with 10% (v/v) fetal calf serum and G418 (400 µg/ml) (Invitrogen). The cells co-transfected with NHERF1/2 were additionally supplemented with hygromycin (600 µg/ml). To maintain high levels of NHE3 expression, the stably transfected cells were "acid loaded" weekly, as described (J. Biol. Chem 268, 25527-25535 (1996)).

Cell Lines. PS120 fibroblasts lack all endogenous plasma membrane NHEs, NHERF1 (minimal expression), NHERF2, NHERF3 and NHERF4. These cells, when stably expressing rabbit NHE3 with a C-terminal VSV-G protein epitope tag and NHERF2, are called PS120/NHE3/NHERF2 cells (or PS120/E3V/NHERF2 cells), as described (stable cell lines made using pcDNA 3.1, G418 and hygromycin, Invitrogen). Caco-2BBe cells express all four members of the NHERF gene family and small amounts NHE3 (Caco-2BBe/3HA-NHE3 cells). Triple HA-tagged rabbit NHE3 was expressed by adenovirus into Caco-2BBe cells for transport and biochemical analysis.

Libraries of functional/structural specific PSSMs. To generate the position specific scoring matrix (PSSM) set for a specific protein function or structure fold, the protein sequences were collected that were known to be related to the function or structure of interest. In the case of the Transmembrane database, the region for PSSM generation was defined with boundaries by TMHHM. For each PSSM set, PSSMs were generated with the collected sequences or the sequences expanded from them using PSI-BLAST. For expansion, each collected sequence is searched against NCBI NR databases by PSI-BLAST (with the option of $-e10^{-3}$ and $-h\ 10^{-6}$). Among the returned sequences, any redundant sequences were filtered out and the sequences whose pair wise identities to a query were more than 90%. For PSSM generation for those expanded sequences, PSI-BLAST (with the option $-h\ 10^{-6}$) was again run. Finally, the entire library was filtered so that all PSSMs in each respective library have less than 40% identity to each other.

Ada-BLAST embedding. For a complete description, see (Hong et al. Adaptive BLAST-A user-defined platform for the study of proteins. www.jiomics.com/index.php/jio/article/view/33/35:1-20). Briefly, with respect to embedded alignments, a single domain PSSM database was used for pair wise comparisons. In brief the query sequence was modified with a "seed" from the PSSM, creating a consistent initiation site. The "seeds" are generated. from the profiles by taking a portion (e.g., 10% in this study, based on the results from our previous studies of the PSSM sequence (e.g., from the N-terminus or C-terminus). This strategy was designed to amplify and encode the alignments possible for any given sequence. Instead of a sliding window, a sliding "seed" was used, a procedure that is similar, yet inverse to the embedding strategies employed by Henikoff (*Protein Sci*. March; 6(3):698-705 (1997)). Since BLAST algorithms are based a "hit and the extension of the hit" approach, the embedded seed creates a consistent initiation site that allows rps-BLAST to extend an alignment even between highly divergent sequences. Ada-BLAST sequence embedding application exploits this similarity among embedded sequences to adaptively avoid expensive computations. Instead of inserting a seed into every position of a query sequence, Ada-BLAST embeds a seed at the query positions where the seed is likely to be extended to an alignment. Briefly, the five basic steps of embedding with Ada-BLAST are: (i) construct a structural, functional, or evolutionarily related library of PSSMs; (ii) find multiple non-overlapping local alignments; (iii) select seed embedding positions in the query sequence; (iv) generate final alignments with seed; and (v) filter out non-significant alignments using coverage and pairwise identity of the alignment.

Human and rabbit NHE-19 sequences were analyzed for structural domain boundaries, and characterized using the SCOP fold-specific libraries, followed by modeling with Modeller (JIOMICS, 2010). One of the criteria used was prediction of a structure that would remain stable when prepared as a synthetic peptide. Ada-BLAST was performed on rabbit NHE3 (NP 001076166.1) analyzed against position PSSMs curated for five functionalities (integral lipid binding, metal binding, peripheral lipid binding, calcium binding and trafficking) (data not shown). Based on these data, five regions were predicted which could be soluble/functional domains: Peptide 1—aa420-460; Peptide 2—aa480-535; Peptide 3—aa568-605; Peptide 4—aa610-650; and Peptide 5—aa660-710.

Adenoviral Constructs/Infection. Caco-2BBe cells which endogenously express the four members of the NHERF gene family and small amounts of NHE3 were transiently infected with triple HA-tagged rNHE3 previously engineered into replication-deficient Adeno-viral shuttle vector ADLOX.HTM under a cytomegalovirus promoter. Caco-2BBe cells were first grown on Transwell filters (Corning) until 12 days post-confluence in "Caco-2 medium." Cells were then treated with serum-free media containing 6 mM EGTA for 2 hours at 37° C. to allow the tight junctions to open, further exposing apical and basolateral surfaces to the virus. Cells were then infected by appropriate amounts of viral particles diluted (109-1010 particles/ml) in serum-free "Caco-2 medium" at 37° C. for 6 hours; then cells were allowed to recover in "Caco-2 medium" over the next 40 hours before transport assays or Western analyses.

Construction and Expression of NHE3 Truncation Mutants. DNA fragments of NHE3/585V, NHE3/605V, NHE3/640V, NHE3/660V and NHE3/690V (the final number in the name of each mutant indicates the C-terminal amino acid number following the truncation) were amplified from pcDNA 3.1 containing the full-length NHE3V (pcDNA 3.1/NHE3V) by PCR to generate HindIII-XhoI fragments. Sense primer was engineered to contain the HindIII restriction site on the 5' end of NHE3. The XhoI restriction site at the junction between NHE3 and the VSVG sequence allowed the design of antisense primers with the internal sequence at the desired sites of truncation and an XhoI site inserted at the 3' end. Amplicons were restricted with HindIII and XhoI and electrophoresed on 1% agarose gels. The DNA fragments were ligated into the pcDNA 3.1/NHE3V expression vector, and selected with G418. Plasmids expressing these C-terminal truncation mutants were verified by restriction analysis and sequencing. The NHE-deficient PS 120 cells were transfected with each plasmid construct using Lipofectamine 2000 (GibcoBRL). Transfected cell lines resistant to G418 (400 µg/ml) and/or to Hygromycin (600 µg/mL), where indicated, were selected for measurement of $Na^+/H^+$ exchange activity by exposing cells to repetitive cycles of acid loading, as described above.

Measurement of $Na^+/H^+$ Exchange. Cellular $Na^+/H^+$ exchange activity in PS 120 cells grown to about 70% confluency on glass coverslips was determined fluorometrically using the intracellular pH-sensitive dye 2',7'-bis(carboxyethyl)5-6-carboxyfluoresceinacetoxymethyl ester (BCECF-AM, 5µM; Molecular Probes, Eugene, Oreg.). As described previously, PS120 cells were exposed to 40 mM $NH_4Cl$ alone or with 4-bromo-A23187 (0.5 µM) during a 15-minute dye loading. Cells were perfused initially with TMA+ solution (130 mM tetramethylammonium chloride, 5 mM KCl, 2 mM $CaCl_2$, 1 mM $MgSO_4$, 1 mM $NaH_2PO_4$, 25 mM glucose, 20 mM HEPES. pH 7.4), before being switched to $Na^+$ solution (130 mM NaCl instead of tetramethylammonium chloride) for the $Na^+$-dependent pHi recovery. At the end of each experiment, the fluorescence ratio was calibrated to pHi using the high potassium/nigericin method. $Na^+/H^+$ exchange activity data were calculated as the product of $Na^+$ dependent changes in pHi times the buffering capacity at each pHi, and individual points shown in the figures are ratios of $Na^+/H^+$ exchange calculated at multiple pHi values using at least three coverslips per condition in a single experiment. Kinetics of $Na^+/H^+$ exchange were analyzed by Hill plot using Origin (Microcal Software) to estimate Vmax and $K'(H^+)i$ in individual experiments. Means+/−S.E.M. were determined from at least three separate experiments.

Statistics. Results were expressed as mean+/−S.E.M., and statistical evaluation was performed using Student's t-test.

Example 1

IRCX-Competing Peptide. To learn more about the function of the IRCX, synthetic peptides were prepared and used to mimic part of the NHE3 C-terminus and act like a dom-neg to disrupt the IRCX. As the first step, parts of the NHE3 C-terminus were designed as peptides based on structural predictions and modeling. As described above, Human and rabbit NHE1-9 sequences were first analyzed for structural domain boundaries, then structural models were generated using their Fold-Specific Position Specific Scoring Matrix Library, followed by modeling with Modeller.

Figure 2:
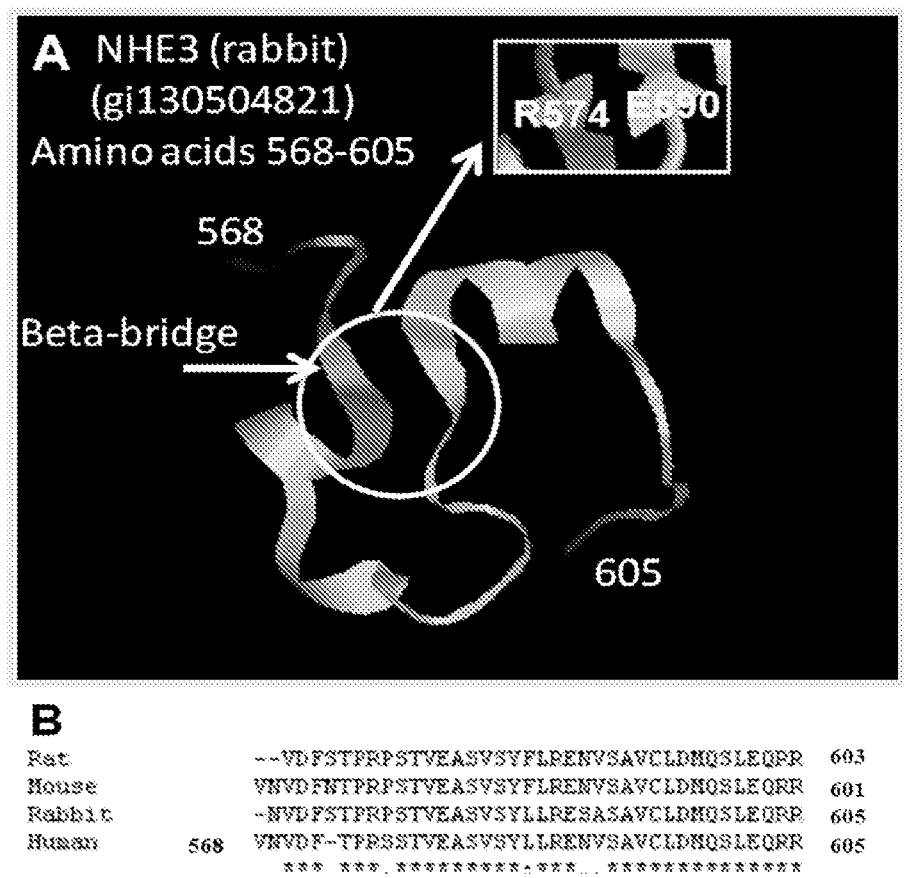
FIG. 2A is an illustration of a putative α-helical-β-bridge structure of IRCX-CP model from Ada-Blast. The insert shows proposed stabilization of helix by pos charge in β-bridge.
FIG. 2B is a portion of the Blast analysis showing conservation of amino acids of this domain of NHE3 across species. (*) identical aa; (:) conserved aa; (.) semi-conserved aa.

The sequence selected for testing (FIG. 2A) consists of rabbit NHE3 aa 568-605. This 38 aa peptide (NVDFST-PRPSTVEASVSYLLRESASAVCLDMQSLEQRR) (SEQ ID NO: 1) is highly conserved in NHE3s across species (FIG. 2B). $D^{569}$ and $R^{574}$ are predicted to be positioned in the β-bridge in a way to stabilize the α-helix by $H^+$ bonding $E^{590}$. The IRCX-CP peptide was synthesized (Peptide 2.0, Chantilly, Va.) with a biotin placed on the N-terminus (HPLC purity 98.54%). To load the peptide into cells, the C-terminus was linked to a positively charged maleimide thiol reactive reagent, Bodipy 577/618 (4,4-difluoro-3,5-bis (4-methoxyphenyl)-8-(4-maleimidylphenyl)-4-bora-3a,4a-diaza-s-indacene, Invitrogen, red fluorescence). Several control peptides were synthesized including a part of the NHE1 C-terminus of similar length that had no predicted tertiary structure and no identified role in NHE1 regulation (major negative control) (100) and a shorter part of this domain of NHE3.

Example 2

Figure 3:
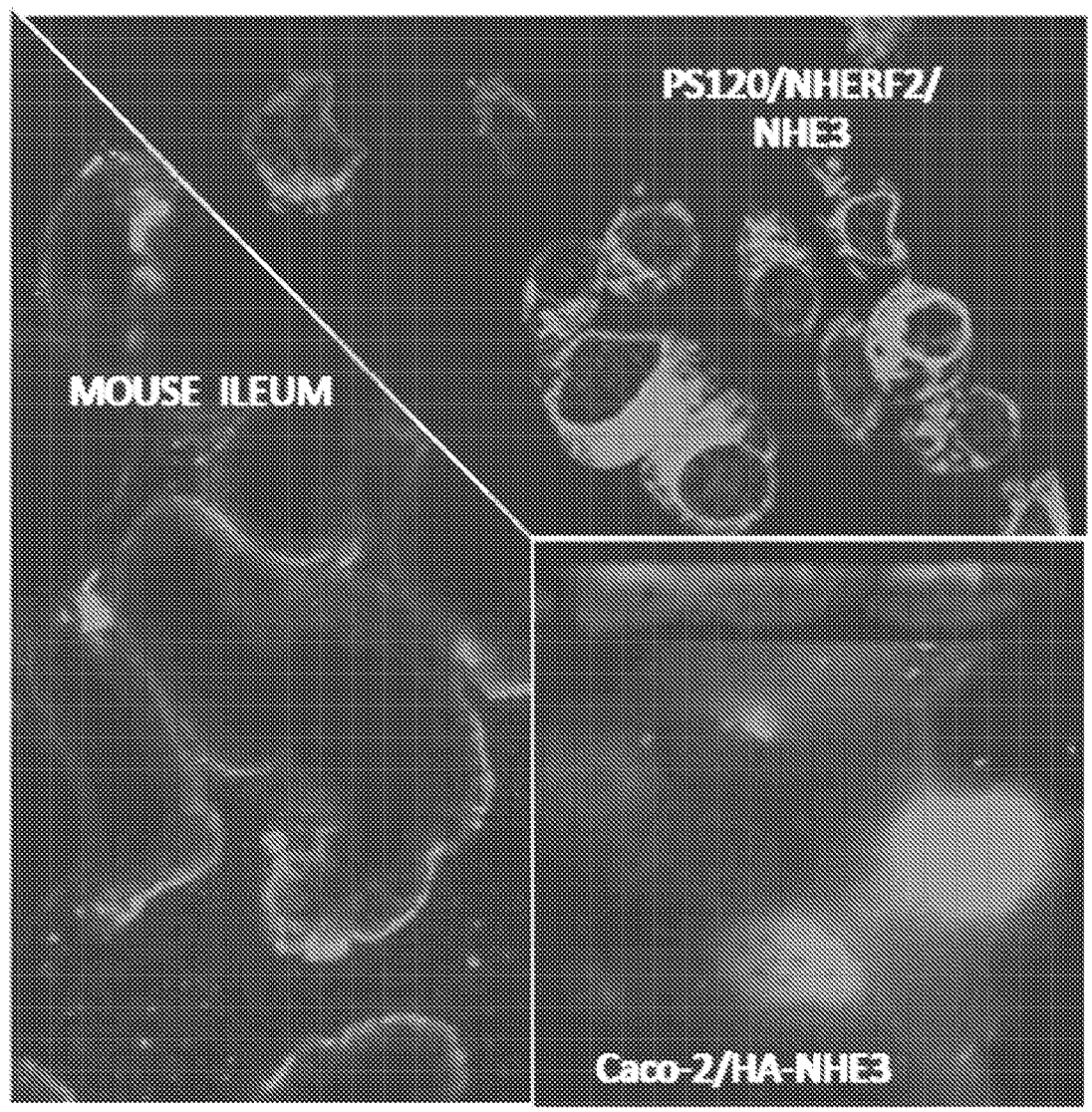
FIG. 3 shows photomicrographs of plasma membrane/intracellular vesicular labeling with Bodipy-IRXC-CP, 400 nM, 15 minutes, at 37° C., in PS120 and Caco-2 cells (above XZ section showing apical labeling and below XY) and mouse ileum.

The fluorescent peptides described above were then loaded into PS120/NHERF2/NHE3, Caco2/NHE3 cells, and mouse small intestine. It was established that loading reaches a maximum in 15 minutes (37° C.) (FIG. 3) and is stable for at least 6 hours. To evaluate the effect of these peptides on NHE3 regulation, PS120 and Caco-2 cells were exposed to 400-1600 nM Bodipy 577/618-peptide and used BCECF/fluorometry to characterize the peptide's effects on basal NHE3 activity and after $Ca^{2+}$ elevation and EGF exposure. In studies in both cell types, all peptide concentrations studied stimulated basal NHE3 activity by about 40%, and reduced $Ca^{2+}$ inhibition of NHE3 by about 50% in PS 120 cells (data not shown) and entirely in Caco-2 cells (FIG. 4A). These effects were maximum at 400 nM, suggesting the peptide effect was at saturation. The peptide without Bodipy did not alter NHE3 activity. Similarly in mouse jejunum studied with BCECF/microscopy in vitro, NHE3 peptide stimulated basal NHE3 activity by 60% and totally prevented NHE3 inhibition by forskolin (FIG. 4B). Also in closed loop in vivo murine jejunum exposed to cholera toxin (1 µg, 6 hours), addition of 400 nM peptide prevented cholera toxin fluid accumulation (FIG. 5). These results have led us to understand that this NHE3 mimetic peptide, IRCX-CP can reverse the inhibitory function of the IRCX, presumably by displacing the inhibitory components from the IRCX complex.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A sodium/hydrogen Exchanger 3 (NHE3) Inhibitory Regulatory Complex ICRX Competing Peptide (ICRX-CP), or a functional portion or analog or derivative thereof.

2. A peptide comprising the amino acid sequence of SEQ ID NO: 1, or a functional portion or analog or derivative thereof.

3. The peptide of claim 1, wherein the peptide binds NHE3 IRCX binding domain or functional portion or fragment thereof.

4. The peptide of claim 3, wherein the NHE3 IRCX binding domain comprises amino acids 568-605 of the NHE3 protein, or a functional portion or fragment thereof.

5. The peptide of claim 1, wherein the peptide stimulates basal NHE3 activity and prevents elevated $Ca^{2+}$ and cAMP inhibition of NHE3.

6. A pharmaceutical composition comprising the peptide of claim 1, and a pharmaceutically acceptable carrier.

7. The pharmaceutical composition of claim 6, further comprising a second therapeutic agent.

8. The pharmaceutical composition of claim 6, wherein the second therapeutic agent is selected from the group consisting of: anti-motility, antidiarrheals, antibiotics, antihelminths, and anti-parasiticals.

9. The pharmaceutical composition of claim 6, further comprising an effective amount of a probiotic composition comprising one or more strains of probiotic microorganisms.

10. A method of treatment of a gastrointestinal disease in a mammal comprising administering to the mammal the peptide of claim 1, or the pharmaceutical composition of claim 6, in an effective amount to modulate or treat the gastrointestinal disease.

11. The method of claim 10, wherein the gastrointestinal disease is selected from the group consisting of acute, prolonged, and chronic diarrhea.

12. The method of claim 11, wherein the gastrointestinal disease is chronic diarrhea.

13. A method for prophylaxis of diarrhea in the gastrointestinal tract of a subject, the method comprising:
    administering to the subject an effective amount of the peptide of claim 1, or the pharmaceutical composition of claim 6, to prevent and/or treat the symptoms of diarrhea in the subject.

14. The method of claim 13, wherein the pharmaceutical composition further comprises a second therapeutic agent.

15. The method of claim 14, wherein the second therapeutic agent is selected from the group consisting of: anti-motility, antidiarrheals, antibiotics, antihelminths, and anti-parasiticals.

* * * * *

```
SEQUENCE LISTING

<160> NUMBER OF SEQ ID NOS: 1

<210> SEQ ID NO 1
<211> LENGTH: 38
<212> TYPE: PRT
<213> ORGANISM: Oryctolagus cuniculus

<400> SEQUENCE: 1

Asn Val Asp Phe Ser Thr Pro Arg Pro Ser Thr Val Glu Ala Ser Val
1               5                   10                  15

Ser Tyr Leu Leu Arg Glu Ser Ala Ser Ala Val Cys Leu Asp Met Gln
            20                  25                  30

Ser Leu Glu Gln Arg Arg
        35
```